(12) United States Patent
Schweikert et al.

(10) Patent No.: US 8,535,279 B2
(45) Date of Patent: Sep. 17, 2013

(54) HUBER NEEDLE WITH SAFETY TUBE

(75) Inventors: Timothy M Schweikert, Levittown, PA (US); Doreen Kibblehouse, Harleysville, PA (US)

(73) Assignee: Medical Components, Inc., Harleysville, PA (US)

( * ) Notice: Subject to any disclaimer, the term of this patent is extended or adjusted under 35 U.S.C. 154(b) by 333 days.

(21) Appl. No.: 12/846,191

(22) Filed: Jul. 29, 2010

(65) Prior Publication Data

US 2011/0028916 A1 Feb. 3, 2011

Related U.S. Application Data

(60) Provisional application No. 61/230,359, filed on Jul. 31, 2009.

(51) Int. Cl.
*A61M 25/00* (2006.01)
*A61M 5/32* (2006.01)

(52) U.S. Cl.
USPC ............................ 604/268; 604/264; 604/272

(58) Field of Classification Search
USPC .................................. 604/263–264, 268, 272
See application file for complete search history.

(56) References Cited

U.S. PATENT DOCUMENTS

| | | |
|---|---|---|
| 4,737,144 A | 4/1988 | Choksi |
| 4,887,998 A | 12/1989 | Martin et al. |
| 5,059,180 A | 10/1991 | McLees |
| 5,300,046 A | 4/1994 | Scarfone et al. |
| 5,322,517 A | 6/1994 | Sircom et al. |
| 5,328,482 A | 7/1994 | Sircom et al. |
| 5,382,240 A | 1/1995 | Lam |
| 5,611,781 A | 3/1997 | Sircom et al. |
| 5,662,610 A | 9/1997 | Sircom |
| 5,697,907 A | 12/1997 | Gaba |
| 5,743,883 A | 4/1998 | Visconti |
| 5,879,337 A | 3/1999 | Kuracina et al. |
| 6,001,080 A | 12/1999 | Kuracina et al. |
| 6,117,108 A | 9/2000 | Woehr et al. |
| 6,254,575 B1 | 7/2001 | Thorne, Jr. et al. |
| 6,280,420 B1 | 8/2001 | Ferguson et al. |
| 6,287,278 B1 | 9/2001 | Woehr et al. |
| 6,443,929 B1 | 9/2002 | Kuracina et al. |
| 6,592,556 B1 | 7/2003 | Thorne |
| 6,595,955 B2 | 7/2003 | Ferguson et al. |

(Continued)

FOREIGN PATENT DOCUMENTS

| | | |
|---|---|---|
| EP | 1430921 | 6/2004 |
| JP | 2004-195227 | 7/2004 |

(Continued)

OTHER PUBLICATIONS

International Application No. PCT/US2010/043691, International Preliminary Report on Patentability, issued Jan. 31, 2012, mailed Feb. 9, 2012, 4 pages.

(Continued)

*Primary Examiner* — Nicholas Lucchesi
*Assistant Examiner* — Rebecca E Eisenberg
(74) *Attorney, Agent, or Firm* — Blank Rome LLP

(57) ABSTRACT

A Huber needle assembly includes a needle, a safety tube substantially around at least a portion of the needle, and a skin plate at one end of the safety tube. The safety tube is adapted to irretractably extend over the needle.

18 Claims, 3 Drawing Sheets

(56) References Cited

U.S. PATENT DOCUMENTS

| | | |
|---|---|---|
| 6,616,630 B1 | 9/2003 | Woehr et al. |
| 6,629,959 B2 | 10/2003 | Kuracina et al. |
| 6,676,633 B2 | 1/2004 | Smith et al. |
| 6,719,721 B1 | 4/2004 | Okazaki et al. |
| 6,796,962 B2 | 9/2004 | Ferguson et al. |
| 6,796,968 B2 | 9/2004 | Ferguson et al. |
| 6,824,530 B2 | 11/2004 | Wagner et al. |
| 6,860,871 B2 | 3/2005 | Kuracina et al. |
| 6,878,136 B2 | 4/2005 | Fleury et al. |
| 6,902,546 B2 | 6/2005 | Ferguson |
| 6,918,894 B2 | 7/2005 | Fleury et al. |
| 6,926,693 B2 | 8/2005 | Enns |
| 6,949,086 B2 | 9/2005 | Ferguson et al. |
| 6,984,213 B2 | 1/2006 | Horner et al. |
| 6,997,902 B2 | 2/2006 | Thorne, Jr. et al. |
| 7,004,927 B2 | 2/2006 | Ferguson et al. |
| 7,008,402 B2 | 3/2006 | Ferguson et al. |
| 7,029,461 B2 | 4/2006 | Ferguson et al. |
| 7,097,637 B2 | 8/2006 | Triplett et al. |
| 7,125,397 B2 | 10/2006 | Woehr et al. |
| 7,144,389 B2 | 12/2006 | Ferguson et al. |
| 7,179,244 B2 | 2/2007 | Smith et al. |
| 7,198,618 B2 | 4/2007 | Ferguson et al. |
| 7,214,211 B2 | 5/2007 | Woehr et al. |
| 7,264,613 B2 | 9/2007 | Woehr et al. |
| 7,341,573 B2 | 3/2008 | Ferguson et al. |
| 7,357,784 B2 | 4/2008 | Ferguson |
| 7,413,562 B2 | 8/2008 | Ferguson et al. |
| 7,438,703 B2 | 10/2008 | Barrus et al. |
| 7,455,664 B2 | 11/2008 | Fleury et al. |
| 7,458,954 B2 | 12/2008 | Ferguson et al. |
| 7,534,231 B2 | 5/2009 | Kuracina et al. |
| 7,549,979 B2 | 6/2009 | Enns et al. |
| 7,569,044 B2 | 8/2009 | Triplett et al. |
| 7,608,057 B2 | 10/2009 | Woehr et al. |
| 7,611,485 B2 | 11/2009 | Ferguson |
| 7,611,487 B2 | 11/2009 | Woehr et al. |
| 7,618,395 B2 | 11/2009 | Ferguson |
| 7,625,360 B2 | 12/2009 | Woehr et al. |
| 7,717,888 B2 | 5/2010 | Vaillancourt et al. |
| 7,762,992 B2 | 7/2010 | Triplett et al. |
| 7,927,314 B2 | 4/2011 | Kuracina et al. |
| 8,002,746 B2 | 8/2011 | Erskine |
| 2003/0114797 A1 | 6/2003 | Vaillancourt et al. |
| 2003/0163098 A1* | 8/2003 | Fleury et al. ............ 604/263 |
| 2004/0049159 A1 | 3/2004 | Barrus et al. |
| 2004/0082922 A1 | 4/2004 | Fleury et al. |
| 2004/0147881 A1 | 7/2004 | Hyun |
| 2006/0129106 A1 | 6/2006 | Ferguson et al. |
| 2007/0282275 A1 | 12/2007 | Ferguson et al. |
| 2008/0097304 A1 | 4/2008 | Thorne |
| 2008/0119795 A1 | 5/2008 | Erskine |
| 2008/0208139 A1 | 8/2008 | Scheurer et al. |
| 2008/0262434 A1 | 10/2008 | Vaillancourt |
| 2009/0062744 A1 | 3/2009 | Weilbacher et al. |
| 2009/0137958 A1 | 5/2009 | Erskine |
| 2009/0249605 A1 | 10/2009 | Erskine |
| 2010/0137815 A1 | 6/2010 | Kuracina et al. |
| 2010/0280413 A1 | 11/2010 | Ferguson et al. |
| 2011/0166526 A1 | 7/2011 | Kuracina et al. |
| 2011/0220274 A1 | 9/2011 | Erskine |

FOREIGN PATENT DOCUMENTS

| | | |
|---|---|---|
| JP | 2004195227 | 7/2004 |
| WO | WO9907424 | 2/1999 |
| WO | 02/087672 | 11/2002 |
| WO | 2006/096633 | 9/2006 |
| WO | 2006/096634 | 9/2006 |
| WO | 2006/096635 | 9/2006 |
| WO | 2006/096636 | 9/2006 |
| WO | 2010/101573 | 9/2010 |

OTHER PUBLICATIONS

International Search Report and Written Opinion; International Application No. PCT/US2010/043691; International Filing Date: Jul. 29, 2010; 5 pages.

* cited by examiner

HUBER NEEDLE WITH SAFETY TUBE

RELATED APPLICATIONS

This application claims benefit of U.S. Provisional Application Ser. No. 61/230,359, filed Jul. 31, 2009, entitled "Huber Needle with Safety Tube," which application is incorporated herein by reference.

FIELD OF THE INVENTION

The present invention relates to needles for subcutaneous injections. In particular, the present invention relates to Huber needles with a safety tube.

BACKGROUND OF THE INVENTION

Known Huber needles are widely used in hospitals and alternate care sites. These needles are often used in conjunction with implanted ports. Such Huber needles provide a non-coring needle that is used to administer chemotherapy, IV fluids, medications, total parenteral nutrition, or to transfuse blood products through implanted ports. The implanted ports contain a self-sealing septum that seals around the needle, holds the needle in place, and allows for multiple accessing by a Huber needle.

The known Huber needle is designed for safety of the patient, however they present a considerable risk to the user of such Huber needles. The known Huber needle, if improperly used, exposes the user to bloodborne pathogens or the drug or medication being administered through the Huber needle. Known Huber needles require two hands to extract the needle from the implanted port. One hand is used to stabilize the implanted port, while the other hand is used to withdraw the needle. The force required to withdraw the needle from the self-sealing septum of the implanted port can cause the needle to rebound and thus a needle stick injury to the user. Such a needle stick injury can result in transfer of a bloodborne pathogen, such as Hepatitis or HIV. Also, healthcare workers that prepare hazardous drugs, mix drugs, or administer drugs are at risk for exposure to the drug. Even when drugs are carefully handled, exposure can result from inhalation or direct skin contact with the drug.

Although several alternate Huber needles are available, a need still exists for a Huber needle with safety features that minimize the risk of exposure to bloodborne pathogens or drugs.

SUMMARY OF THE INVENTION

Accordingly, it is an aspect of the present invention to provide a Huber needle with a safety tube.

An exemplary embodiment of the present invention provides a Huber needle assembly. The Huber needle assembly includes a needle, a safety tube substantially around at least a portion of the needle, and a skin plate at one end of the safety tube. The safety tube is adapted to extend over the needle.

Other objects, advantages and salient features of the invention will become apparent from the following detailed description, which, taken in conjunction with the annexed drawings, discloses a preferred embodiment of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE ILLUSTRATED EMBODIMENTS

Referring to FIGS. 1-9, the present invention provides a Huber needle assembly 100 that substantially minimizes the risk of exposure to bloodborne pathogens, drugs, and any other undesirable article, living or non-living, that can be transported through the air or by direct contact. The Huber needle assembly 100 includes a safety tube 102 that can irretractably extend over a needle 104 as it is extracted. Thus, the safety tube 102 substantially prevents the transmission of bloodborne pathogens, drugs, and any other undesirable article, living or non-living.

Figure 1:
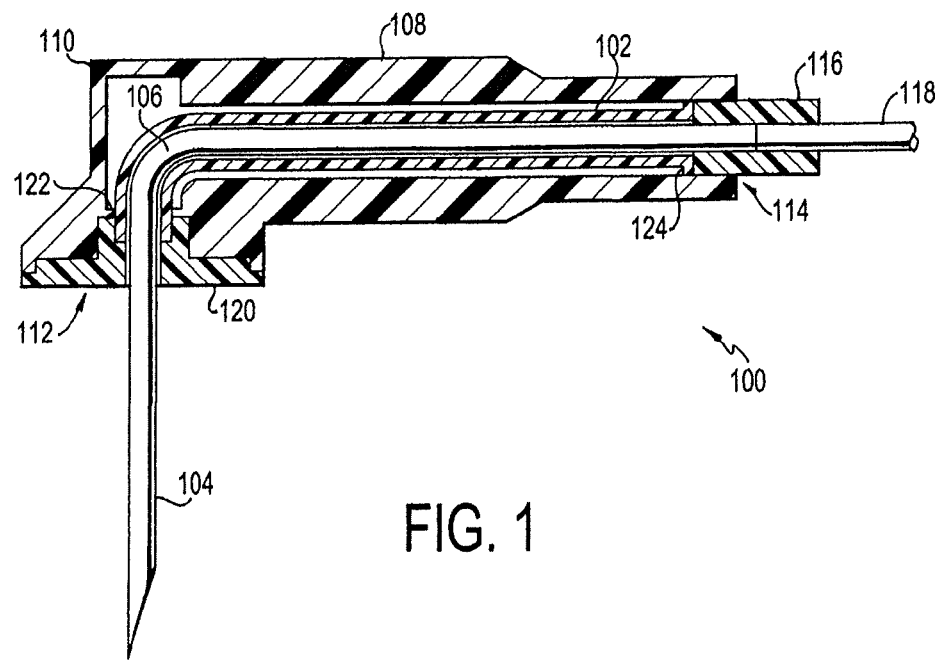
FIG. 1 is a side sectional elevational view of a Huber needle assembly according to an embodiment of the present invention.

Turning to FIG. 1, one embodiment of the Huber needle assembly 100 is shown in a sectional view. The Huber needle assembly 100 includes, at least, the needle 104 and the safety tube 102 that substantially surrounds a portion of the needle 104. In the depicted embodiment, the needle 104 includes a bent portion 106 that is substantially a 90° elbow to facilitate the inserting and extracting of the needle 104. In alternate embodiments, the needle 104 may lack the bent portion 106, have several bent portions 106, or have a bent portion 106 that is not a substantially 90° elbow. The depicted needle 104 also has a substantially circular cross-sectional shape, but in alternate embodiments, the needle 104 can have a cross-sectional shape that is oval-like, triangular, rectangular, polygonal, or combinations of the aforementioned. The needle 104 can be made of any suitable material, such as stainless steel.

The Huber needle assembly 100 can also include a body 108 that substantially surrounds the safety tube 102 when the safety tube 102 is not extended over the needle 104. The body 108 provides mechanical support and protection for, at least, the unextended safety tube 102. Because the body 108 substantially surrounds the unextended safety tube 102, the body 108 can have any desired shape that provides a hollow to receive the unextended safety tube 102. In the embodiment shown, the body 108 has a generally tubular shape with a bent portion 110. Also, the depicted body 108 has a first end 112 and a second end 114 at opposed ends of the body 108. The needle 104 extends from the first end 112, and a coupling 116 is disposed at the second end 114.

The coupling 116 mates the needle 104 to another tube 118. The tube 118 provides a pathway for drugs, solutions, compounds, blood, or some other substance to be delivered through the needle 104. The depicted tube 118 also has a substantially circular cross-sectional shape to generally match the cross-sectional shape of the needle 104, but in alternate embodiments, the tube 118 can have any suitable cross-sectional shape and be made of any suitable material that provides a suitable pathway for drugs, solutions, compounds, blood, or some other substance to be delivered through the needle 104. Also, although the depicted coupling 116 mates one tube 118 with the needle 104, in other embodiments, the coupling 116 can mate more than one tube 118 with the needle 104.

When the safety tube 102 is not extended, the safety tube 102 is substantially disposed between the first end 112 and the second end 114 of the body 108. As shown in the figure, the safety tube 102 has a generally tubular shape that can accept a portion of the needle 104. However, in alternate embodiments, the safety tube 102 can have any suitable shape that can accept a portion of a needle 104 and extend over the needle 104. The safety tube 102 includes a skin plate 120.

The safety tube 102 has a first end that attaches to the skin plate 120, and a second end that is disposed within the body 108. The safety tube 102 also has a stopping mechanism that prevents the safety tube 102 from exiting the body 108 completely when extracted. In one embodiment, the safety tube 102 can include one or more retaining rings. In the embodiment shown in FIG. 1, the safety tube 102 has a retaining ring 124 at the second end 114 of the safety tube 102. Another retaining ring 122 is disposed at the first end 112 of the body 108, near in location, or adjacent to, the skin plate 120. The retaining rings 122, 124 stop further extension of the safety tube 102, as it is being extended over the needle 102. Thus, the retaining rings 122, 124 prevent the safety tube 102 from being decoupled from the body 108.

Figure 2:
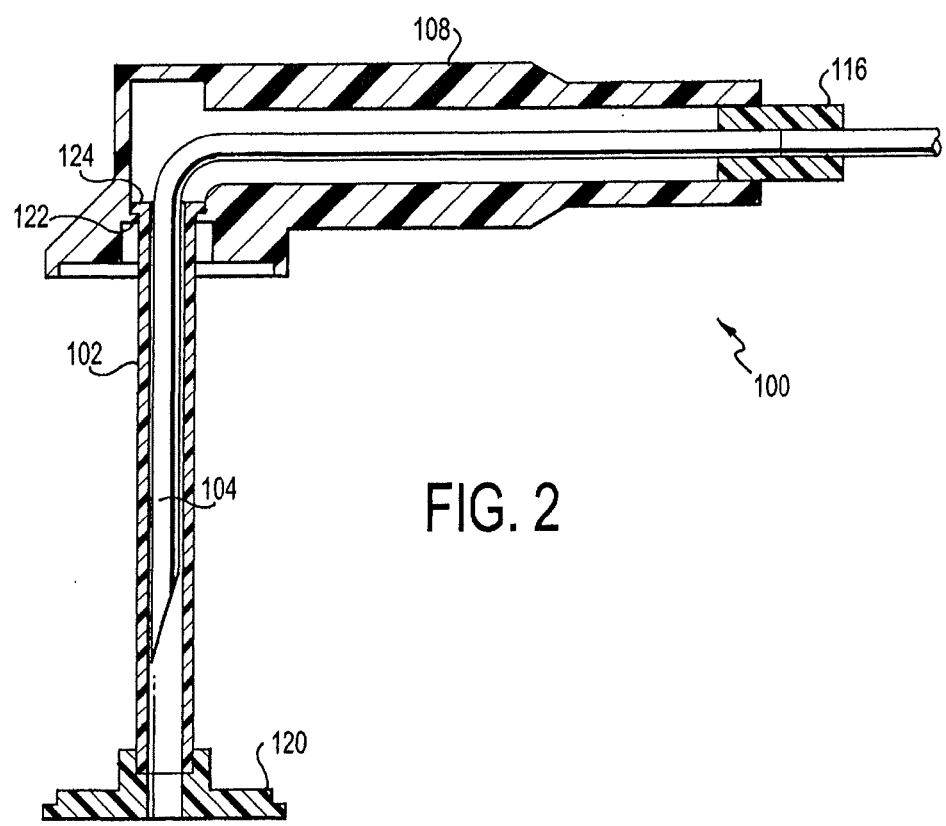
FIG. 2 is a side sectional elevational view of the Huber needle assembly illustrated in FIG. 1 with a safety tube extended.

Referring to FIG. 2, the Huber needle assembly 100 is shown with the safety tube 102 substantially extended over the needle 104. As shown in the figure, as the safety tube 102 is being extended, one of the retaining rings 124 is coupled to the safety tube 102 and moves with the safety tube 102, while the other retaining ring 122 is substantially fixed to the body 108. When the retaining ring 124 moving with the safety tube 102 abuts the other retaining ring 122, the retaining rings 122 and 124 prevent the safety tube 102 from extending further and prevent the safety tube 102 from separating from the body 108.

Figure 3:
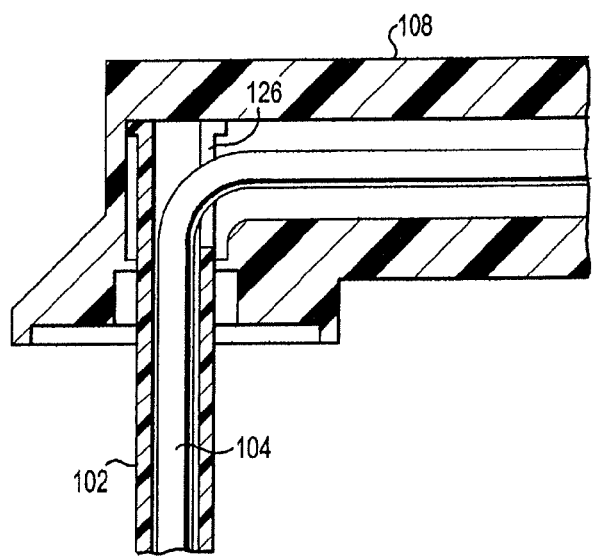
FIG. 3 is a portion in detail of the side sectional elevational view of the Huber needle assembly illustrated in FIG. 2 with the safety tube extended.
Figure 4:
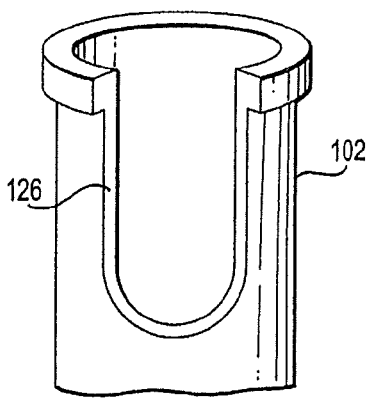
FIG. 4 is top perspective view of the safety tube illustrated in FIG. 2.

The safety tube 102 is configured that when it is fully extracted over the needle 104, it is not capable of retracting back into the body 108 and re-expose the needle 104 tip. Referring to FIG. 3, a portion of the needle 104 with the safety tube 102 substantially extended over the needle 104 is shown with the safety tube 102 shown in cross section. As shown in the figure, the safety tube 102 can include a slot 126. Because the needle 104 has a bent portion 106, the safety tube 102 can include a slot 126 that allows the safety tube 102 to extend over the bent portion 106 of the needle 104. Referring to FIG. 4, a portion of the safety tube 102 is shown in detail. The slot 126 can have a size that slightly larger than the diameter of the needle 104. The slot 126 when extracted pass the bend portion 106 of the needle 104 prevents the safety tube to retract into the body 108. When pushed backwards, such as in a potential needle stick situation, the horizontal portion of the needle passes into the slot 126 and the top part of the body cavity abuts the second end of the safety tube 102 preventing it from making the bend and fully retracting into the body 108.

Figure 5:
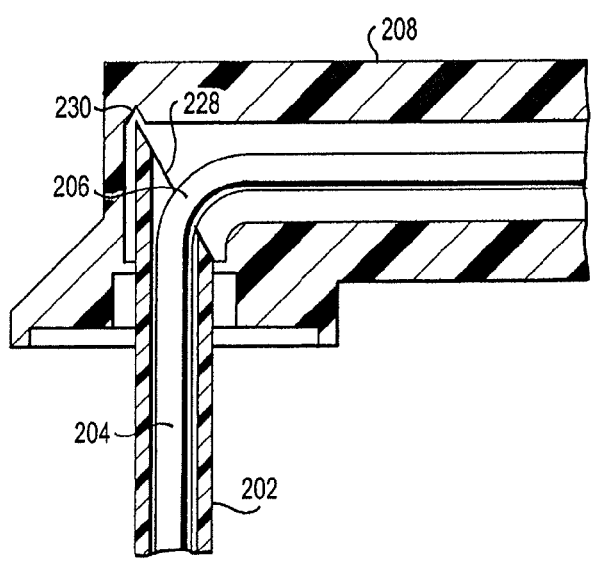
FIG. 5 is a portion in detail of a side sectional elevational view of the Huber needle assembly according to another embodiment of the present invention.

Referring to FIG. 5, a portion of a safety tube 202 according to another embodiment is shown. Unlike the safety tube 102 shown in FIGS. 1-4, the safety tube 202 does not have a retaining ring 124 or a slot 126. Instead, as shown in the figure, the safety tube 202 can have a bevel 228. The needle 204 and the body 208 are substantially similar to the needle 104 and the body 108 of FIGS. 1-4; thus, a detailed description thereof is omitted. The body 208 can also include a capture portion 230 that can accept a tip of the bevel 228. In general, a depression in the top of the body cavity generally can serve as the capture mechanism, such as the exemplary capture portion 230 shown in FIG. 5. When the safety tube 202 is extracted over the bend portion 206 of the needle 204, the tip of the bevel 228 is aligned with, or translated into, the capture portion 230. When the safety tube 202 is pushed backward, such as in a potential needle stick situation, the tip of the bevel 228 abuts, or moves further into, the capture portion 230, thereby preventing the safety tube 202 from making the bend and fully retracting into the body 208.

Figure 6:
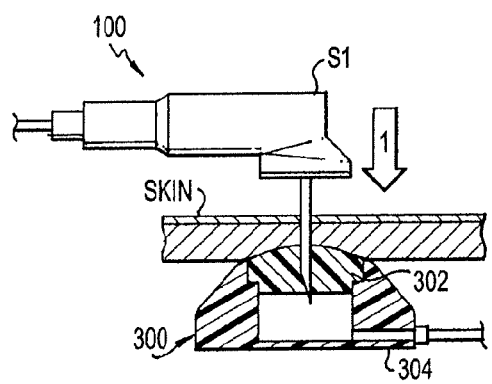
FIG. 6 is a side elevational view of the Huber needle assembly illustrated in FIG. 1 as it is being inserted towards an infusion port shown in a sectional view.
Figure 7:
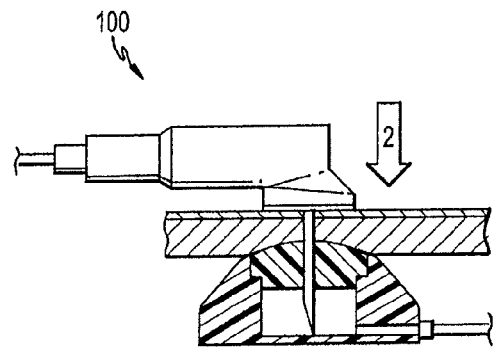
FIG. 7 is a side elevational view of the Huber needle assembly illustrated in FIG. 1 fully inserted.

Referring to FIGS. 6-9, the Huber needle assembly 100 is shown being inserted and withdrawn from a subcutaneous infusion port 300. Turning to FIG. 6, the Huber needle assembly 100 is shown being inserted through the skin to the subcutaneous infusion port 300. As shown in the figure, the safety tube 102 is not extended over the needle 104, as the needle 104 is pushed towards the infusion port 300 in the direction of arrow "1". Referring to FIG. 7, the Huber needle assembly 100 is shown with the needle 104 fully inserted and the Huber needle assembly 100 resting against the skin. Thus, after the Huber needle assembly 100 has been pushed further in the direction of arrow "2", the needle 104 has pierced the port septum 302 of the infusion port 300 so that one end of the needle 104 rests in the port reservoir 304.

Figure 8:
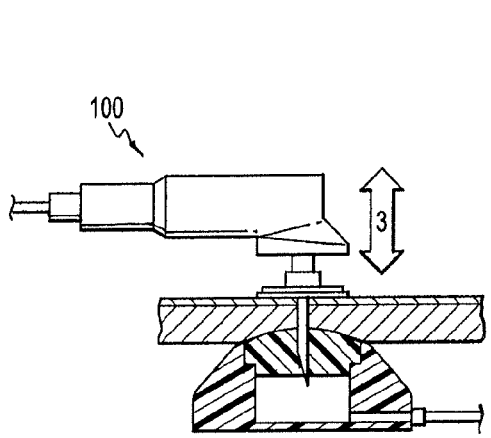
FIG. 8 is side elevational view of the Huber needle assembly illustrated in FIG. 1 as it is being withdrawn from an infusion port.

Referring to FIG. 8, the needle 104 of the Huber needle assembly 100 is shown being withdrawn. The user of the Huber needle assembly 100 pushes the skin plate 120 against the skin in one direction as the rest of the Huber needle assembly 100 is pulled away from the infusion port 300 in the opposite direction, as defined by arrow "3". The user holds down the wings 128 of the skin plate 120 so that the skin plate 120 remains substantially against the skin. With the other hand, the user pulls the remaining parts of the Huber needle assembly 100 away from the skin plate 102 and the infusion port 300. Because the user is holding the skin plate 120 against the skin with one hand and pulling the rest of the Huber needle assembly 100 away from the skin with the other hand, the safety tube 102 is extended. Thus, the safety tube 102 is extended over the needle 104 as the needle 104 is pulled away from the infusion port 300 along with the rest of the Huber needle assembly 100.

Figure 9:
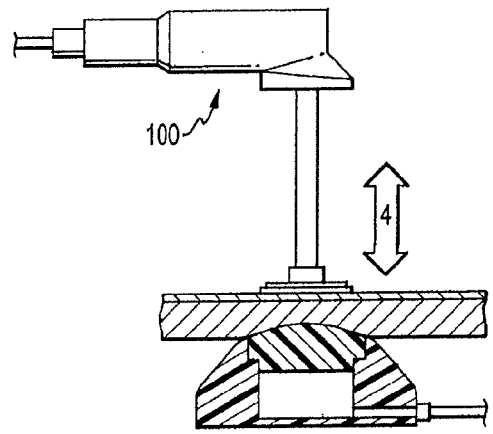
FIG. 9 is side elevational view of the Huber needle assembly illustrated in FIG. 1 fully withdrawn.

Referring to FIG. 9, the needle 104 of the Huber needle assembly 100 is shown fully withdrawn. As shown in the figure, the needle 104 is fully withdrawn from the infusion port 300 in one direction while the safety tube 102 is extended over the needle 104 in the opposite direction as defined by arrow "4". The safety tube 102 substantially extends over the needle 104, and thus the needle 104 can be totally encompassed within the safety tube 102. Thereafter, the needle 104 can be removed from the Huber needle assembly 100 and safely disposed. Because the needle 104 is encompassed within the safety tube 102, the Huber needle assembly 100 minimizes the risk of accidental needle stick to a user or a patient. It also minimizes the risk of inhaling any emissions arising from the substance traveling through the needle 104.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:

1. A Huber needle assembly, comprising:
a body having a first end and a second end;
a needle extending from the first end of the body;
a skin plate; and
a safety tube substantially disposed around at least a portion of the needle, the safety tube having a first end attached to the skin plate and a second end disposed within the body, wherein the safety tube is adapted to irretractably extend over the needle,
wherein the second end of the safety tube includes a bevel and a top part of a cavity of the body includes a capture portion, wherein the capture portion is configured to capture the bevel, upon extraction of the safety tube, to prevent the safety tube from retracting into the body.

2. The Huber needle assembly of claim 1, further comprising a stopping mechanism that prevents the safety tube from exiting the body when extracted.

3. The Huber needle assembly of claim 2, wherein the stopping mechanism includes a retaining ring at the second end of the safety tube and a retaining ring disposed at the first end of the body, wherein the retaining rings prevent the safety tube from being decoupled from the body.

4. The Huber needle assembly of claim 2, wherein the stopping mechanism includes a retaining ring attached to the second end of the safety tube and a retaining ring disposed at the first end of the body, wherein, during extraction of the safety tube, the retaining ring attached to the second end of the safety tube moves with the safety tube and abuts the retaining ring disposed at the first end of the body, upon full extraction of the safety tube, to prevent the safety tube from separating from the body.

5. The Huber needle assembly of claim 2, wherein the stopping mechanism includes a retaining ring attached to the second end of the safety tube and a retaining ring disposed at the first end of the body, wherein, during extraction of the safety tube, the retaining ring attached to the second end of the safety tube moves with the safety tube and abuts the retaining ring disposed at the first end of the body, upon full extraction of the safety tube, to prevent the second end of the safety tube from exiting the body.

6. The Huber needle assembly of claim 1, wherein the needle comprises a bent portion disposed within a cavity of the body, and the second end of the safety tube comprises a slot that allows the safety tube to extend along and around the bent portion of the needle.

7. The Huber needle assembly of claim 6, wherein the second end of the safety tube abuts a top part of the cavity of the body, after extraction of the safety tube along and around the bent portion of the needle, to prevent the safety tube from retracting into the body.

8. The Huber needle assembly of claim 1, wherein the needle comprises a bent portion disposed within the cavity of the body, and wherein the capture portion is located in a top part of the cavity of the body adjacent to the bent portion.

9. A Huber needle assembly, comprising:
a body having a cavity therethrough, the cavity and the body together having a first end and a second end;
a needle having a length disposed within at least a portion of the cavity of the body and a length extending from the first end of the cavity of the body;
a safety tube substantially disposed along and around the needle, where the safety tube, in a first position, extends along and around at least a portion of the length of the needle within the cavity of the body and where, in the first position, the length of the needle extending from the first end of the cavity of the body is exposed, and where the safety tube, in a second position, irretractably extends along and around an entirety of the length of the needle extending from the first end of the cavity of the body, whereby the entirety of the length of the needle extending from the first end of the cavity of the body, in the second position, is totally encompassed within the safety tube; and
a stopping mechanism that prevents the safety tube from exiting the cavity of the body when extracted.

10. The Huber needle assembly of claim 9, wherein the safety tube is tubular in shape to extend along and around the needle.

11. The Huber needle assembly of claim 9, further comprising a skin plate, and wherein the safety tube has a first end attached to the skin plate and a second end disposed within the cavity of the body, the second end of the safety tube being disposed within the cavity of the body whether the safety tube is in the first position or in the second position.

12. The Huber needle assembly of claim 9, wherein the stopping mechanism includes a retaining ring at the second end of the safety tube and a retaining ring disposed at the first end of the cavity of the body, wherein the retaining rings interact to prevent the safety tube from being decoupled from the body.

13. The Huber needle assembly of claim 9, wherein the stopping mechanism includes a retaining ring attached to the second end of the safety tube and a retaining ring disposed at the first end of the cavity of the body, wherein, during extraction of the safety tube, the retaining ring attached to the second end of the safety tube moves with the safety tube within the cavity of the body and abuts the retaining ring disposed at the first end of the cavity of the body to prevent the second end of the safety tube from exiting the body.

14. The Huber needle assembly of claim 9, wherein the needle comprises a bent portion disposed within the cavity of the body, and the second end of the safety tube comprises a slot that allows the safety tube to extend along and around the bent portion of the needle.

15. The Huber needle assembly of claim 9, wherein the needle comprises a bent portion disposed within the cavity of the body, the second end of the safety tube comprises a slot that allows the safety tube to extend along and around the bent portion of the needle, and the second end of the safety tube abuts a top part of the cavity of the body, adjacent to the bent portion of the needle, after extraction of the safety tube along and around the bent portion of the needle to prevent the safety tube from retracting back into the cavity of the body and re-exposing a tip of the needle.

16. The Huber needle assembly of claim 9, wherein the second end of the safety tube includes a bevel and a top part of a cavity of the body includes a capture portion, wherein the capture portion is configured to capture the bevel, upon extraction of the safety tube, to prevent the safety tube from retracting into the body.

17. A Huber needle assembly, comprising:
- a body having a cavity therethrough, the cavity and the body each comprising a first end and a second end, the cavity of the body further comprising a top part;
- a needle comprising a first length extending from the first end of the cavity of the body, a second length disposed within at least a portion of the cavity of the body, and a tip; and
- a safety tube substantially disposed along and around the needle, the safety tube comprising a first end and a second end, the safety tube being longitudinally translatable between an unextracted position within the cavity of the body in which the first length of the needle is exposed, and an extracted position in which the safety tube totally encompasses an entirety of the first length of the needle,
- wherein the second end of the safety tube abuts the top part of the cavity of the body when the safety tube is in the extracted position, so that the safety tube is not capable of retracting back into the cavity of the body and re-exposing the tip of the needle.

18. The Huber needle assembly of claim 17, wherein the needle further comprises a bent portion disposed within the cavity of the body, the second end of the safety tube comprises a slot that facilitates the safety tube extending along and around the bent portion of the needle so that the second end of the safety tube abuts the top part of the cavity of the body, adjacent to the bent portion of the needle, after extraction of the safety tube along and around the bent portion of the needle to prevent the safety tube from retracting back into the cavity of the body and re-exposing the tip of the needle.

* * * * *